Figure 1:
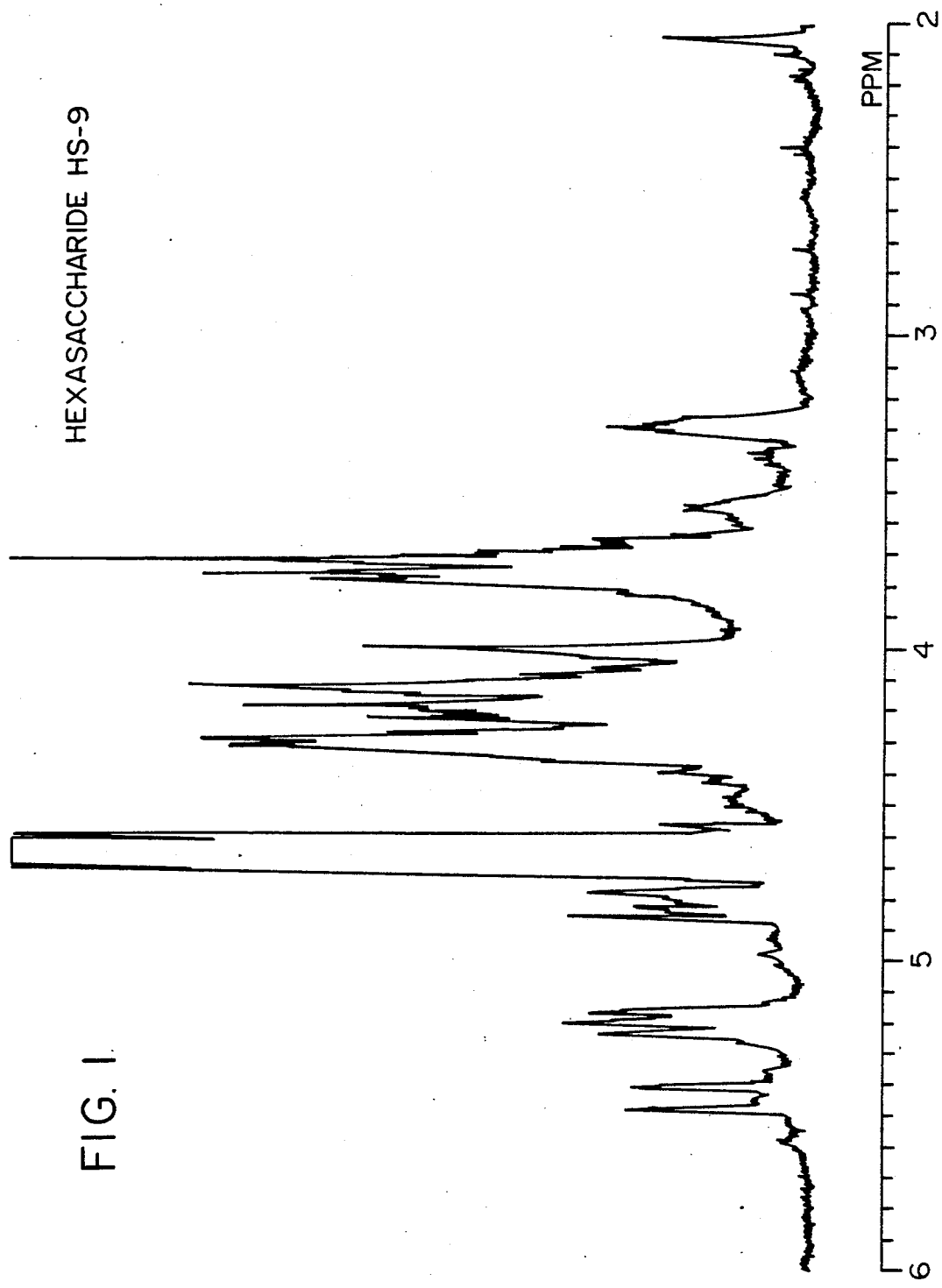

United States Patent [19]

Bergendal et al.

[11] Patent Number: 5,039,529

[45] Date of Patent: Aug. 13, 1991

[54] NOVEL HEPARIN DERIVATIVES

[75] Inventors: Karin H. L. Bergendal, Danderyd; Rolf A. Johansson, Huddinge; Carl M. E. Svahn, Sollentuna, all of Sweden

[73] Assignee: KabiVitrum AB, Stockholm, Sweden

[21] Appl. No.: 306,020

[22] PCT Filed: May 2, 1988

[86] PCT No.: PCT/SE88/00282

§ 371 Date: Jan. 27, 1989

§ 102(e) Date: Jan. 27, 1989

[87] PCT Pub. No.: WO88/09347

PCT Pub. Date: Dec. 1, 1988

[30] Foreign Application Priority Data

May 27, 1987 [SE] Sweden ............................. 8702254

[51] Int. Cl.$^5$ ...................... A61K 33/34; A61K 33/32
[52] U.S. Cl. .................................... 424/630; 424/639; 424/641; 424/682; 514/56; 536/21
[58] Field of Search ............... 424/630, 639, 641, 646, 424/682; 514/56; 536/21

[56] References Cited

FOREIGN PATENT DOCUMENTS

| 890622 | 3/1958 | Fed. Rep. of Germany . |
| 3027928 | 9/1981 | Fed. Rep. of Germany . |
| 2417859 | 9/1984 | Fed. Rep. of Germany . |
| 2176200 | 12/1986 | Fed. Rep. of Germany . |
| 6853M | 4/1969 | France . |
| 7808487-8 | 12/1986 | Sweden . |

OTHER PUBLICATIONS

"Physiocochemical Properties of Heparin, and its Interaction with Cu(II) and Calcium in Relation to Anticoagulation", S. S. Stivala, Stevens Institute of Technology, Federation Proceedings, vol. 36, No. 1, Jan. 1977, pp. 83-88.
"Angiogenic Factors", Judah Folkman and Michael Klagsbrun, Science, vol. 235, Jan. 23, 1987, pp. 442-447.
Archives of Biochemistry and Biophysics, vol. 122, 1967, pp. 40-54, S. S. Stivala et al.: "Physiocochemical Studies of Fractionated Bovine Heparin IV Cu(II) Binding in Relation to pH, Molecular Weight, and Biological Activity".
Chemical Abstracts, vol. 101, 1984, ref. No. 168321h; Columbus, Ohio, US; G. Allesandri, et al.: "Angiogenesis in Vivo and Selective Mobilization of Capillary Endothelium In Vitro by a Heparin-Copper Complex".
Cancer Research, vol. 43, No. 4, Apr. 1983, pp. 1790-1797, G. Alessandri, et al., "Mobilization of Capillary Endothelium In Vitro Induced by Effectors of Angiogenesis In Vivo".
Analytical Letters, vol. 15, No. B16, 1982, pp. 1277-1288; Marcel Dekker Inc., E. Grushka, et al., "The Binding of Cu(II) and An(II) Ions by Heparin".
Journal of the National Cancer Institute, vol. 69, No. 5, Nov. 1982, pp. 1183-1188, K. S. Raju, et al., "Ceruloplasmin, Copper Ions, and Angiogenesis".
Chemical Abstracts, vol. 78, 1973, ref. No. 81230k; Columbus, Ohio, US; B. Lages, et al., "Interaction of the Polyelectrolyte Heparin with Copper (II) and Calcium".
Chemical Abstracts, vol. 79, 1973, ref. no. 40438m; Columbus, Ohio, US; B. Lages, et al.: "Copper Ion (List continued on next page.)

Primary Examiner—John W. Rollins
Attorney, Agent, or Firm—Pollock, Vande Sande & Priddy

[57] ABSTRACT

A novel complex of (a) a metal ion selected from copper, calcium, manganese, iron, and zinc ions, and (b) a fraction of heparin, heparan sulfate, low molecular weight heparin, low molecular weight heparan sulfate, heparin fragments, heparan sulfate fragments, and oligosaccharides derived from heparin or from heparan sulfate, or a salt of such fractions which fractions bind to the said metal ion, said complex containing from 5 to 1,000 nmole metal of component (a) per $\mu$mole of component (b).

17 Claims, 1 Drawing Sheet

OTHER PUBLICATIONS

Binding and Heparin Interactions of Human Fibrinogen".
Chemical Abstracts, vol. 96, 1982, p. 74, ref. No. 818e; Columbus, Ohio, US; S. S. Stivala et al.: "Ultrasonic Relaxation Studies of Heparin Solutions and the Binding of Copper (II) to Heparin".
Chemical Abstracts, vol. 94, 1981, p. 189, ref. No. 42930z; Columbus, Ohio, US; J. W. Park, et al.: "Spectroscopic Studies on Copper (2+) and Calcium (2+) Binding with Glucosaminoglycans".
Chemical Abstracts, vol. 90, 1979, p. 210, ref. No. 17940n; Columbus, Ohio, US; D. C. Mukherjee, et al.: "Optical Properties of Copper (II) Complexes with Heparin and Related Glycosaminoglycans".
Chemical Abstracts, vol. 98 (1983) abstract No. 158493w (Allessandri, G. et al).
Chemical Abstracts, vol. 98 (1983) abstract No. 49058n (Grushka, E. et al.).
Chemical Abstracts, vol. 98 (1983) abstract No. 14974f (Raju, N. et al.).
Chemical Abstracts, vol. 86, abstract No. 83359y (Stivala, S. S. et al.).
Chemical Abstracts, vol. 67 (1967) abstract No. 115406n (Stivala, S. S. et al.).
Chemical Abstracts, vol. 100 (1984) abstract No. 187636k (Grant, D. et al.).

NOVEL HEPARIN DERIVATIVES

FIELD OF THE INVENTION

The present invention relates to novel complexes of metal ions as defined below, in particular copper ions, with such fractions of heparin, heparan sulfate, low molecular weight heparin, low molecular weight heparan sulfate, heparin fragments, heparan sulfate fragments, and oligosaccharides derived from heparin or heparan sulfate that specifically bind to such metal ions, or a salt of such fractions, to a process for obtaining such metal-binding fractions and metal complexes thereof, and to the use of such complexes in therapy. It was unexpectedly found that the *inhibitory* properties on angiogenesis of these novel complexes of the invention in vivo in presence of a suitable angiostatic agent, especially a steroid were markedly enhanced with respect to such fractions that were not bound to metal ions and also with respect to the unfractionated products.

BACKGROUND OF THE INVENTION

It has been shown that a combination of heparin or a hexasaccharide fragment together with a suitable steroid cause inhibition of angiogenesis in mammals and that tumor masses in mammals are caused to regress and metastasis is prevented (Folkman et al.; Science 1983, 221, 719-725). It was also shown that this combination was effectively inhibiting other angiogenesis depending processes such as fertilization of the rat (Folkman et al., European Patent Application No. EP-0114589). It is also effective in reducing osteoporosis and in treating deseases involving neovascularization, such as neovascular diseases of the eye. Also because of the occurrence of angiogenesis in psoriasis and arthritis, it is expected that this combination will be useful in treating those diseases.

Whereas further research and development with respect to the steroid part of this combination that inhibits angiogenesis has yielded more potent and specific steroids (Crum et al., Science 1985, 230, 1375-1378), no such progress has been made with regards to the heparin component of the heparin steroid composition. A synthetic highly sulfated non-anticoagulant pentasaccharide was recently shown to possess inhibiting effect on angiogenesis in the presence of a steroid to the same extent as its highly anticoagulant active analogue (the 3-O-sulfated analogue) (Choay et al., European Patent Application No. EP-0140781). This finding further supports the finding that the anticoagoulant (anti-Xa) properties of heparin and heparin fragments are not required for the heparin and heparin fragments to be inhibitory on angiogenesis in the presence of steroids (Folkman et al., Science 1983, 221, 719-725; Crum et al., Science 1985, 230, 1375-1378).

Heparin is a glycosidically linked highly sulfated copolymer of uronic acids and D-glucosamine. The uronic acids being L-iduronic acid or D-glucuronic acid of which the former usually is sulfated and the latter usually nonsulfated. The glucosamine is either N-sulfated or N-acetylated and also frequently 6-O-sulfated. Small amounts of other structural variants also occur. The exact structure of heparin and the precise nature of its antithrombotic mechanism of action has not been elucidated although it has been in widespread use for almost 50 years. Heparin is polydisperse with a molecular weight range from 3,000-30,000 with many structural variations within a given chain. The exact composition of heparin varies depending on its source, which usually is porcine intestinal mucosa, bovine lung, bovine intestinal mucosa, or ovine intestinal mucosa and also depending on the method for its preparation and purification. Low molecular weight heparin (molecular weight range 2,000-10,000) has been isolated in small amounts by fractionation of standard heparin. Heparin fragnents of molecular weight range 500-10,000 has been prepared by partial depolymerization of heparin by chemical or enzymatic methods. Chemical depolymerization has been carried out in many different ways, frequently by nitrites at low pH, by alkaline β-elimination usually after esterification of uronic acids or by oxidative methods usually using peroxides or periodate. After depolymerization with nitrites the newly formed anhydromannose at the reducing end of the heparin fragments and the oligosaccharides derived from such a fragment usually are reduced to anhydromannitol or oxidized to anhydromannonic acid for increased stability of the product. The enzymatic depolymerization and the alkaline β-elimination results in the same 4,5-unsaturation in the nonreducing end of the heparin fragments and in the oligosaccharides derived from these fragments. For increased stability such unsaturated groups can subsequently be reduced by standard procedures for example catalytic hydrogenation, or the whole 4,5-unsaturated monosaccharide may be eliminated by for example mild acid treatment or by applying metal containing reagents such as mercury salts. In the latter case heparin fragments, heparan sulfate fragments, and oligosaccharides derived from them containing an uneven number of saccharide moieties are obtained. Heparan sulfate is the only other glycosaminoglycan besides heparin that also contains N-sulfated glucosamines. Most heparan sulfate however contains more N-acetylated glucosamine than N-sulfated glucosamine, the opposite being the case for heparin.

The same methods of fractionation and depolymerization used for heparin are also applicable to heparan sulfate. The enzyme used for heparan sulfate is usually a hepartitinase (heparanase) instead of heparinase which is most commonly used for heparin. Small amounts of heparan sulfate is usually found in standard heparins. Heparan sulfate also constitutes a large part of heparin by-products particularly form bovine lung.

Heparin by itself (without a steroid) enhances the intensity of angiogenesis induced by tumors and by tumor derived factors in vivo, although in the absence of tumor cells or tumor extracts or tumor derived factors neither heparin nor the mast cells which release heparin could induce angiogenesis (Taylor and Folkman, Nature 1982, 297, 307-312).

Some angiogenic factors from normal cells and tissue, for example so-called heparin binding growth factors can also induce angiogenesis and stimulate the growth of capillary endothelial cells. With some growth factors, this stimulation of capillary endothelial cell growth is potentiated by heparin.

Heparin, by virtue of its high negative charge, has a strong affinity for cations, where the binding generally is ionic since pH dependency is usually observed. Clinically used standard heparin is either the sodium or calcium salt of heparinic acid. The calcium heparin usually has a calcium content of about 11 w/w % which corresponds to about 2.8 μmole $Ca^{2+}$/mg heparin. For cupric ions ($Cu^{2+}$), binding to heparin was shown to be pH-dependent and for a typical heparin (molecular weight 13100, anticoagulant activity 146 IU/mg) copper binding was 0.606 μmole $Cu^{2+}$/mg heparin at neutral pH (Stivala SS, Fed. Proc. Fed. Am. Soc. Exp. Bio. 1977, 36, 83–88). Thus cupric ions bind to a lesser extent to heparin than calcium ions at neutral pH, showing for cupric ions about 20% of the binding of that of the calcium ions. Heparin containing 1 μg of copper per 20 μg of heparin (which corresponds to 0.787 μmole $Cu^{2+}$/mg heparin or about 10 μmole $Cu^{2+}$/μmole heparin) has been shown to be able to *induce* angiogenesis in vivo, which heparin by itself could not do (Alessandri G. Raju K, Gullino P M, Microcirculation, Endothelium and Lymphatics 1984, 1, 329–346).

Metal chelate affinity chromatography, also called ligand exchange chromatography or immobilized metal ion adsorption, is usually carried out by binding (chelating) various metal ions, such as for example $Cu^{2+}$, $Zn^{2+}$, $Ni^{2+}$, $Co^{2+}$, $Mn^{2+}$, $Ca^{2+}$, $Fe^{2+}$ and $Fe^{3+}$ to a solid matrix, for example a cation exchange resin or a special metal ion chelator such as Chelating Sepharose ® 6B Pharmacia and Chelex ™ 100 Bio-Rad and then carry out fractionation of complex mixtures.

DESCRIPTION OF THE INVENTION

It has been found according to the present invention that complexes of certain metal ions, especially copper ions but also calcium, manganese, iron, and zinc ions, with such fractions of heparin, heparan sulfate, low molecular weight heparin, low molecular weight heparan sulfate, heparin fragments, heparan sulfate fragments, and oligosaccharides derived from heparin or from heparan sulfate, or a salt of such fractions which fractions specifically bind to such metal ions, exhibit markedly enhanced anti-angiogenic properties when used in conjunction with an angiostatic component, especially a steroid as disclosed above. The present invention accordingly relates to novel complexes of copper, calcium, manganese, iron, and zinc ions with such fractions of heparin, heparan sulfate, low molecular weight heparin, low molecular weight heparan sulfate, heparin fragments, heparan sulfate fragments, and oligosaccharides derived from heparin or from heparan sulfate which bind to such metal ions, a process for the preparation of the said novel complexes the use of the said novel complexes of the invention in therapy especially in conjunction with an angiostatic component, especially a so-called angiostatic steroid component the use of the novel complexes of the invention in conjunction with an angiostatic component, especially a so-called angiostatic steroid in the treatment of ailments where reduced angiogenesis is desired the said novel metal-binding fractions of heparin, heparan sulfate, low molecular weight heparin, low molecular weight heparan sulfate, heparin fragments, heparan sulfate fragments, and oligosaccharides derived from heparin or heparan sulfate, and salts thereof a method for the treatment of such ailments where reduced angiogenesis is desired by administration of a therapeutically effective amount of the novel complex of the invention in conjunction with an angiostatic component, especially a so-called angiostatic steroid the use of the novel complexes of the invention in the preparation of a medicament for the treatment of such ailments where reduced angiogenesis is desired pharmaceutical compositions containing a novel complex of the invention optionally in conjunction with an angiostatic component, especially a so-called angiostatic steroid.

Although in the following reference will be made mainly to complexes with copper ions ($Cu^{2+}$, $Cu^+$), it is understood that also complexes with calcium ($Ca^{2+}$) manganese ($Mn^{2+}$), iron ($Fe^{2+}$-$Fe^{3+}$) and zinc ($Zn^{2+}$) ions are included.

The new fractions of this invention contain constituents of heparin and/or heparan sulfate. They are isolated from heparins and heparan sulfates of bovine, porcine, ovine, or other orgin, low molecular weight heparins or heparan sulfates, fragments of heparins and of heparan sulfate, oligosaccharides from any of these products and also such oligosaccharides which are size homogenous and from other fractions containing heparin or heparan sulfate constituents, for example "by-products" from heparin production. The new fractions of the invention will contain from 2 to about 120 sugar moieties corresponding to molecular weights from 500 to about 35,000. With "salts" of the said heparin fragments is meant physiologically acceptable salts such as sodium, calcium or ammonium salts. The sodium and calcium salts, especially the sodium salt are the preferred salts. Normally, the heparin complexes of the invention will be used in the form of a salt thereof.

The new fractions of the invention are characterized by that they are retained by copper ions chelated to a solid matrix and in that they can be desorbed from this copper ion-containing solid matrix by a pH-gradient, or a competitive ligand or other chelating agents. They may also be produced in this way from the starting materials described above.

The content of copper ions will be in the range of from 5 to 1,000 nmole per μmole of the heparin/heparan sulfate component. A preferred interval will be from 10 to 1,000 nmole per μmole of the heparin/heparan sulfate component. Among the copper binding fractions of the heparin/heparan sulfate component it will be preferred to use low molecular weight heparin or low molecular weight heparan sulfate having a molecular weight of from 500 to 10,000 or from 500 to 8,000 and low molecular weight oligosaccharides derived from heparin or from heparan sulfate, especially tetrasaccharides, hexasaccharides, octasaccharides, decasaccharides, dodecasaccharides, tetradecasaccharides and hexadecasaccharides.

Angiogenesis, the growth of new capillary blood vessels, is important in normal processes such as development of the embryo, formation of the corpus luteum and wound healing. It is also a component in pathologic processes such as chronic inflammation, certain immune responses and neoplasia. Angiogenesis is also a property of most solid tumours and is necessary for their growth.

Medical indications where reduced angiogenesis is desired may be exemplified with
- tumours, especially solid tumours
- prevention of metastasis
- neovascular diseases of the eye, such as retrolental fibroplasia, diabetic retinopathy, and neovascular glaucoma
- osteoporosis
- psoriasis
- arthritis.

The novel complexes of the present invention are preferably intended for use in conjunction with an angiostatic component, especially a so-called angiostatic steroid (Crum et al., Science Vol. 230, p. 1377), that is a steroid with high anti-angiogenic effect and low glucocorticoid and mineralo-corticoid effect. Examples of such steroids are given by Crum et al. and include cortisone
hydrocortisone
11α-isomer of hydrocortisone
6α-fluoro-17,21-dihydroxy-16β-methyl-pregna-4,9,(11)diene-3,20-dione
17α-hydroxy-progesterone.
5β-pregnane-3α,17α,21-triol-20-one (Tetrahydro-S)
tetrahydrocortisol or its 3α-glucuronide In clinical practice, administration of the novel complexes of the present invention will be made essentially as is prescribed for standard heparin and for low molecular weight heparin. Thus, topical and parenteral administration—i.v., subcutaneous, intramuscular—are foreseen. Local administration e.g. in the eye or to a tumour may be desired. In addition, the novel complexes of the present invention can be administered orally.

The steroid component is administered in a manner which is customary for administration of steroids, such by the oral or parenteral route.

The novel complexes of the invention and the angiostatic component may be mixed together prior to administration or may be administered separately.

The amount to be administered of the novel complex of the invention and of the angiostatic component must be adjusted to the individual need of each patient.

For preparing the novel complexes of the invention, heparin, heparan sulfate, low molecular weight heparin, low molecular weight heparan sulfate, a heparin fragment, a heparan sulfate fragment, or an oligosaccharide derived from heparin of from heparan sulfate, or a salt thereof, is reacted with a metal ion selected from copper, calcium, mangan, iron, and zinc ions, followed by isolation of the complex thus formed.

The reaction can be carried out by means of an ion exchange resin, especially a resin containing iminodiacetic acid groups, or in solution. The reactants are adapted so that the complex obtained will contain in the case of copper ions from 5 to 1,000 nmole copper per μmole of the heparin/heparan sulfate component. Similar amounts will be desired for the other metal complexes of the invention.

For preparing and isolating the new fractions of this invention metal chelate affinity chromatography has been carried out using a solid matrix containing iminodiacetic acid groups for binding (chelating) the metal ions (Chelex TM 100, Bio-Rad or Chelating Sepharose ® 6B Pharmacia). By using a solution of cupric chloride ($CuCl_2$) as a source of copper ions the copper ions chelated should be mainly cupric ions ($Cu^{2+}$). Some of the copper ions may however be present as cuprous ions ($Cu^+$). To a column charged with copper ions the sample to be fractionated was applied dissolved in distilled water, a buffer solution, a salt solution or a buffer-salt solution. The column was then washed with the same solvent which was used to dissolve the sample. Material that was not bound to, or very little bound to the copper Chelex column was collected in this fraction. For desorption of applied products that was bound to (retained by) the column three general methods was used:

1. Desorption by a pH gradient. As it has been shown that heparin copper interaction was dependent on pH, this is a valid alternative.

2. Desorption, by an increasing gradient or isocratically by a competitive ligand such as imidazole, histamine, glycine, aquous ammonia, an ammonium salt, preferably ammonium chloride, or a solution containing metal ions of the same kind, which have been bound to the matrix. The solution of the ligand preferably contains the salt and/or the buffer used in the washing step.

3. Desorption by a chelating agent such as EDTA or EGTA which will strip the metal ions from the gel and cause the elution of all the adsorbed material.

Ligand exchange chromatography using copper ions has been applied to protein, amino acids and nucleotides, but not previously to complex carbohydrates such as heparin or heparan sulfate or products derived from them. When heparin, heparan sulfates or their fragments, low molecular weight products, or the size homogenous oligosaccharides derived from those products or biproducts from heparin manufacturing were fractionated by copper chelate affinity chromatography, it was found that a small part of these products became bound to the copper ions on the matrix. After desorption of these tightly bound fractions they were assayed for inhibition of angiogenesis together with hydrocortison or an other angiostatic steroid, as described by Folkman et al., Science 1983, 221, 719–725, Crum et al., Science 1985, 230, 1375–1378. It was then unexpectedly found that those fractions which had been retained by (bound to) copper ions on the matrix showed higher inhibitory effects on angiogenesis in the presence of a so-called angiostatic steroid than the fractions of these products that was not retained by (bound to) the copper ion containing matrix. (Table 1.)

The fractions retained on the copper Chelex column also showed higher inhibitory effect on angiogenesis in presence of a so-called angiostatic steroid (for example hydrocortison) than the respective starting products which were used for the fractionation. (Table 1.)

Clinically used standard heparin according to the U.S. Pharmacopeia and the British Pharmacopeia must not contain more than 30 ppm of heavy metals. By atomic absorption analysis it was found that in heparin, heparan sulfate and the low molecular weight materials, fragments, fractions and oligosaccharides prepared form heparin and heparan sulfate up to about 10 ppm of these heavy metals was copper. However, within this 0–10 ppm of copper, no correlation between content of copper and degree of inhibition of angiogenesis in the presence a steroid was obvious.

When the fractions eluted from the copper Chelex column were treated with Chelex containing sodium ions, it was found that the first fraction which was eluted with water, a salt solution, a buffer solution, or a buffer-salt solution always contained less than 20 ppm of copper as determined by atomic absorption spectroscopy. However, the binding fractions which were desorbed as described above, after treatment with Chelex containing sodium ions always contained more copper (see Table 2). This residual amount of copper could only be removed with great difficulty, for example by dialysis against large amounts of a solution of EDTA (see Example 9). It was then unexpectedly found that this residual amount of copper ions in the fractions which had been bound to (retained by) the copper Chelex column was necessary for the improved inhibition of angiogenesis shown by these fractions. On the removal of this residual amount of copper ions, the anti-angiogenic activity was lost (see Table 2). Addition of copper ions to these binding fractions depleted of copper ions restored their anti-angiogenic activity (see Table 2).

When copper ions were added to an unretained fraction (containing 5 ppm of copper) in an amount that was found to be effective in the binding fraction from the same separation, no increase but rather a decrease in anti-angiogenic activity was observed (see Table 2).

The new fractions of heparin, heparan sulfate and the fractions of products derived from them are characterized by that they show enhanced inhibition of angiogenesis in the presence of an angiostatic steroid that they have a capacity of binding a certain amount of copper ions strongly that they in addition of having a capacity of binding a certain amount of copper ions strongly also must contain enough copper ions to match this capacity in order to show enhanced inhibition of angiogenesis.

The enhanced inhibition of angiogenesis in the presence of an angiostatic steroid is shown in the egg assay (Table 1). The strong binding of copper ions is shown by the high affinity of these fractions for a copper Chelex column, e.g. not being eluted by a water solution, a high salt solution, corresponding to a 0.5M to 2M or 3M solution of NaCl, or a high salt solution of a neutral or almost neutral buffer solution. Strong copper binding is also shown by the difficulty to remove copper ions from these fractions once they have bound the copper ions, e.g. treatment by a copper chelating agent such as a Chelex column in sodium form did not remove the strongly bound copper ions. These were only removed by very extensive treatment with the strong metal chelating agent EDTA. The amount of copper ions necessary for the new fractions to show enhanced inhibition of angiogenesis is determined by the amount of structural elements in these fractions that give rise to the enhanced inhibition of angiogenesis. Copper ions in excess to this amount (e.g. copper ions which bind to less specific structures) have no additional enhancing effect to the inhibition of angiogenesis of these fractions, but rather a deleterious effect possibly due to a rather high toxicity of copper ions. For a heparin fragment prepared according to Example 1 (e.g. HF-3) an optimal level of copper ions is between 10–500 nmol per $\mu$mol binding fraction.

TABLE 1

Inhibition of angiogenesis by heparin, heparin fragments and oligosaccharides from heparin fragments in presence of hydrocortison

| Example | Product | Amount $\mu$g | Percent inhibition[1] | Anti-Xa U/mg |
|---|---|---|---|---|
| 2 | Tetrasacch. (TS-1) | | | |
| 2 | Tetrasacch. (TS-2) | | | |
| 2 | Tetrasacch. (TS-3) | | | |
| 2 | Hexasacch. (HS-1) | 25 | 24 | |
| 2 | Hexasacch. (HS-2) | 25 | 24 | |
| 2 | Hexasacch. (HS-3) | 25 | 48 | |
| 1 | Heparin fragment (HF-1) | 50 | 33 | 90 |
| 1 | Heparin fragment (HF-2) | 50 | 30 | |
| 1 | Heparin fragment (HF-3) | 50 | 57 | 16 |
| 3 | Heparin fragment (HF-4) | 12.5 | 28 | |
| 3 | Heparin fragment (HF-5) | 12.5 | 15 | |
| 3 | Heparin fragment (HF-6) | 12.5 | 70 | |
| 4 | Heparin (H-1) | 50 | 56 | 138 |
| 4 | Heparin (H-2) | 50 | 38 | |
| 4 | Heparin (H-3) | 50 | 72 | 119 |
| 4 | Heparin (H-3) | 50 | 17[2] | |
| 4 | Heparin (H-1) | 5 | 10 | 138 |
| 4 | Heparin (H-2) | 5 | 12 | |
| 4 | Heparin (H-3) | 5 | 36 | 119 |
| 5 | Tetrasacch. (TS-4) | 25 | 21 | |
| 5 | Tetrasacch. (TS-5) | 25 | | |
| 5 | Tetrasacch. (TS-6) | 25 | 24 | |
| 5 | Tetrasacch. (TS-7) | 25 | 48 | |
| 6 | Hexasacch. HS-4 | 25 | 9 | |
| 6 | Hexasacch. HS-5 | 25 | 10 | |
| 6 | Hexasacch. HS-6 | 25 | 12 | |
| 6 | Hexasacch. HS-7 | 25 | 19 | |
| 6 | Hexasacch. HS-8 | 25 | 22 | |
| 6 | Hexasacch. HS-9 | 25 | 57 | |
| 7 | Decassach. DS-1 | 25 | 26 | |
| 7 | Decasacch. DS-2 | 25 | 13 | |
| 7 | Decasacch. DS-3 | 25 | 54 | |

[1]For details see experimental part
[2]Without hydrocortison

TABLE 2

Inhibition of angiogenesis in the presence of hydrocortison by fractions of heparin and heparin fragments according to the invention. The importance of residual copper ions in these fractions.

| Compound | | $\mu$g | nmol | Percent inhibition | Copper ppm | nmole copper $\mu$mole compound |
|---|---|---|---|---|---|---|
| Binding fraction | HF-3 | 50 | 8.3 | 57 | 255 | 24 |
| of Heparin fragment | HF-3A[1] | 50 | 8.3 | 8 | 5 | 0.48 |
| (MW 6000) | HF-3B[1] | 50 | 8.3 | 37 | 100 | 9.5 |
| | HF-3C[1] | 50 | 8.3 | 32 | 645 | 61 |
| | HF-3E[1] | 50 | 8.3 | 53 | 1100 | 104 |
| | HF-3D[1] | 50 | 8.3 | 70 | 1500 | 142 |
| Heparin fragment[2] | HF-2[1] | 50 | 6.3 | 30 | 5 | 0.64 |
| (MW 8000) | HF-2A[1] | 50 | 6.3 | 8 | 160 | 20 |
| Binding fraction of | H-3 | 50 | 3.8 | 72 | 220 | 46 |
| Heparin | H-3 | 12.5 | 0.96 | 42 | 220 | 46 |
| (MW 13000) | H-3A[1] | 12.5 | 0.96 | 19 | 40 | 8.2 |
| | H-3B[1] | 12.5 | 0.96 | 38 | 690 | 142 |
| | H-3C[1] | 12.5 | 0.96 | 19 | 1100 | 226 |
| Heparin[2] | H-2 | 50 | 3.8 | 38 | 2 | 0.4 |
| | H-2A | 50 | 3.8 | 18 | 200 | 42 |

[1]HF-3A was obtained by eliminating strongly bound copper ions from HF-3 (see experimental part. Example 9). HF-3B, HF-3C, HF-3D and HF-3E were obtained by addition of various amounts of cupric (Cu$^{2+}$)chloride to HF-3A. HF-2A was obtained by addition of the appropriate amount of cupric (Cu$^{2+}$)chloride to HF-2. HF-3A was obtained by eliminating strongly bound copper ions from H-3. H-3B and H-3C was obtained by addition of cupric (Cu$^{2+}$)chloride to H-3A. H-2A was obtained by addition of the appropriate amount of cupric (Cu$^{2+}$)chloride to H-2.
[2]Non-binding fraction.

EXAMPLE 1

Copper binding heparin fragment from heparin fragment obtained by alkaline β-elimination Sodium heparin from porcine intestinal mucosa (40 g) was dissolved in water (200 ml) and added dropwise while stirring to a solution of Hyamin®1622-[Diisobutylphenoxyethoxyethyl]-dimethylbenzylammonium chloride (200 g) in water (1,000 ml). The mixture was stirred for an additional hour and then cooled in a refrigerator overnight. The supernatant was separated and the precipitate was washed with water (800 ml) and centrifuged for ½ hour. The precipitate was dried at 60° C. in vacuum overnight. The sticky gum obtained was dissolved in dichloromethane (750 ml) and α-bromotoluene (85 ml) was added. This solution was stirred for 72 h at 23° C. The benzylester formed was then precipitated by addition of sodium acetate dissolved in methanol (15 w/v, 1,000 ml). The precipitate was centrifugated for ½ hour, washed with methanol (500 ml) and centrifugated again. The precipitate obtained was dissolved in water (100 ml) and methanol (25–100 ml). Sodium acetate (15 g) was then added. After stirring for ½ h the mixture was filtered through Celite and methanol (1,000 ml) was added to the filtrate. The precipitate was finally washed with methanol, centrifugated and dried in vacuum overnight. Yield of heparin benzylester 26 g.

Heparin benzylester (1.0 g) was dissolved in water (5 ml) and heated to 60° C. Sodium hydroxide (0.40M, 5 ml) was added and the solution was stirred for 1½ h at 60° C. After cooling the mixture to room temperature, a cation exchange resin (Dowex 50 W-X8H) was added to neutralize the basic solution. The resin was filtered off and washed with water (1 ml). The pH of the combined solutions (filtrate and washings) was adjusted to pH 7 by addition of dilute sodium hydroxide and then freeze-dried. Yield 1.0 g. The average molecular weight of this heparin fragment (HF-1) was 8,000 as determined by gel filtration on Sephadex G-75, using heparin fragments of known degree of polymerization as references. Anticoagulant activity was measured by an anti-Xa assay utilizing the chromogenic substrate S-2222 (Kabi Diagnostica Stockholm, Sweden), according to Andersson et al., Thromb. Res. 1979, 15, 531. The anti-Xa activity of this heparin fragment (HF-1) was 90 U/mg.

A copper chelate affinity chromatography column was prepared in the following way. Chelex 100 (Bio-Rad) 50 ml in sodium form was added to a solution of cupric ($Cu^{2+}$) chloride (500 ml, 0.5M). The mixture was left for 24 h and then filtered. The affinity gel was washed with distilled water (3×100 ml). The affinity gel was poured into distilled water and deaerated. A column was prepared by pouring Chelex 100 containing sodium ions (5 ml) into a chromatographic column (25×1.6 cm) and on top of this gel the copper Chelex gel. The column was washed with ammonia (100 ml, 0.5M) and water (250 ml). Heparin fragment (HF-1) (5 g), obtained from heparin by alkaline β-elimination as described above was dissolved in water (20 ml) and applied to the top of the copper Chelex column. Water was used as an eluent at 1.2 cm/h and when no more heparin fragment was eluted as detected by a UV-monitor fixed at 240 nm, the eluent was changed to aqueous ammonia (2M). The solvent was evaporated under vacuum from the fraction eluted by water and the fraction eluted with ammonia. They were then dissolved in distilled water and treated with Chelex 100 containing sodium ions, filtered and freeze-dried. From the water solution, a fraction (3.2 g) of the original heparin fragment was obtained. This fraction, designated Heparin fragment HF-2, had very low, or no affinity for the copper Chelex column. The fraction that eluted with aqueous ammonia was dissolved in distilled water and subjected to ultrafiltration on a Diaflo membrane 5 YCO5 in an Amicon 8050 ultrafilter cell. The retentate was then freeze-dried. The freeze-dried product was dissolved in sodium chloride (2M) and again subjected to ultrafiltration on the same filter, washed thoroughly with water until free from chloride ions and then freeze-dried to give the fraction of the original heparin fragment that had been retained on the copper Chelex column 0.2 g. This fraction of the heparin fragment HF-1 was designated heparin fragment HF-3. The retained fraction HF-3 had an average molecular weight of 6,000 as determined by gel filtration on Sephadex G-75. By elemental analysis N was 2.4% and sulfur 9.5%, and Cu 255 ppm. Uronic acids were 30 w/w % as determined by the carbazol sulfuric acid method according to Bitter and Muir, Anal. Biochem. 1962, 4, 330.

The anti-Xa activity of this heparin fragment (HF-3) was 16 U/mg. Fraction HF-3 did only contain glucosamine and no galactosamine as determined by amino acid analysis. A $^1$H-NMR spectra in $D_2O$/NaOD did not show any signal at 2.7 ppm due to H-2 of glucosamine having a free amino group in that position.

EXAMPLE 2

Copper binding oligosaccharides obtained from oligosaccharides which were obtained from a heparin fragment produced by alkaline β-elimination depolymerization of sodium heparin Sodium heparin from porcine intestinal mucosa (40 g) was dissolved in water (200 ml) and added dropwise while stirring to a solution of Hyamine®1622[-(diisobutylphenoxyethoxyethyl)-dimethylbenzylammonium chloride] (200 g) in water (1,000 ml). The mixture was stirred for an additional hour and then centrifugated. The supernatant was separated and the precipitate was washed with water (800 ml) and centrifugated for ½ hour. The precipitate was dried at 60° C. in vacuum overnight. The sticky gum obtained was dissolved in dichloromethane (750 ml) and methyl iodide (45 ml) was added. This solution was stirred for 72 h at 23° C. The methylester formed was then precipitated by addition of sodium acetate dissolved in methanol (15% w/w, 1,000 ml). The precipitate obtained was dissolved in water (100 ml) and methanol (25–100 ml). Sodium acetate (15 g) was then added. After stirring for ½ h the mixture was filtered through Celite and methanol (1,000 ml) was added to the filtrate. The precipitate was centrifugated and the supernatant decanted. This procedure was repeated until a precipitate was obtained, which was completely water soluble. The precipitate was finally washed with methanol, centrifugated and dried in vacuum overnight. Yield of heparin methylester 23 g.

Heparin methylester (1.0 g) was dissolved in water (5 ml) and heated to 60° C. Sodium hydroxide (0.40M, 5 ml) was added and the solution was stirred for 1½ h at 60° C. After cooling the mixture to room temperature, a cation exchange resin (Dowex 50 W-X8H) was added to neutralize the basic solution. The resin was filtered off and washed with water (1 ml). The pH of the combined solutions was adjusted to pH 7 by addition of dilute sodium hydroxide and then freeze-dried. Yield 0.98 g. The average molecular weight of this heparin fragment was 3,500.

This heparin fragment (MW 3,500) (1 g) was dissolved in sodium chloride (0.25M, 5 ml) and applied to a gel permeation column (5×180 cm P-6, Bio-Rad). The column was eluted by sodium chloride (0.25M) at 5.8 cm/h, using UV-detection at 214 nm. Fractions were collected and desalted on Sephadex G-10 using water at 3.6 cm/h as eluent and detection by refractive index measurement. After freeze-drying, the following fractions were obtained:

| | |
|---|---|
| Disaccharides | 5 mg |
| Tetrasaccharides | 36 mg |
| Hexasaccharides | 65 mg |
| Octasaccharides | 89 mg |
| Decasaccharides | 118 mg |
| Dodecasaccharides | 95 mg |
| Tetradecasaccharides | 71 mg |
| Hexadecasaccharides | 83 mg |
| Octadecasaccharides and higher saccharides | 305 mg |

Tetrasaccharides (TS-1, 450 mg) obtained as described above were dissolved in water (5 ml) and applied to a copper Chelex column, prepared as described in Example 1. Elution was carried out at 1.2 cm/h with water as eluent and monitored with UV-detection at 240 nm. When the unretained (non binding) tetrasaccharides had been eluted, the eluant was changed to aqueous ammonia (2M) that yielded a fraction of tetrasaccharides that had been retained by (bound to) the column. These two fractions were evaporated. The binding fraction was evaporated repeatedly. After evaporation of solvent the fractions were dissolved in distilled water and treated with Chelex containing sodium ions, filtered and purified by chromatography on Sephadex G-10 as described for the isolation of the tetrasaccharides above. After freeze-drying, a tetrasaccharide fraction was obtained from the elution with water, which was very little, or not at all retained on the copper Chelex column. Yield 435 mg (TS-2). The elution with ammonia gave another fraction. This fraction contained tetrasaccharides retained by (bound to) the copper Chelex column. Yield 6.5 mg (TS-3).

In the same way hexasaccharides (HS-1, 550 mg) obtained as described above, from heparin fragment obtained by alkaline $\beta$-elimination of heparin, were fractionated on the copper Chelex column as described above to give a hexasaccharide fraction that was very little, or not at all retained. Yield 526 mg (HS-2). Also a hexasaccharide fraction was obtained, yield 8.9 mg (HS-3) which had been retained on the copper Chelex column. Neither the retained tetrasaccharide (TS-3), nor the retained hexasaccharide (HS-3) showed any $^1$H-NMR signal in $D_2O$/NaOD at 2.7 ppm due to H-2 of glucosamine having a free amino group at that position.

Each one of the larger oligosaccharides was fractionated in the same way as for the tetra- and hexasaccharides except that desalting was performed on an ultrafilter membrane Diaflo 5YCO5 (Amicon Corp.). Yields of the fractions which were retained on the copper Chelex column were 0.3-3%.

EXAMPLE 3

Copper binding heparin fragment from heparin fragment obtained by partial depolymerization of sodium heparin by nitrous acid Sodium heparin from porcine intestinal mucosa was partially depolymerized at pH 1.5 by nitrous acid formed in situ by addition of a solution of sodium nitrite (5% w/w). Anhydromannose groups were then reduced at 3° C. by an excess of sodium borohydride. After destruction of excess sodium borohydride by acetic acid and neutralizing the solution by addition of dilute sodium hydroxide, a portion of the solution was subjected to gel permeation chromatography on Sephadex G-15, with water as an eluent. A heparin fragment (Heparin fragment HF-4), containing tetradeca to hexadecasaccharides as the main components according to HPLC gel-permeation chromatography, was collected, HPLC gel permeation chromatography was done on two TSK G 3,000 SW columns, each 600 mm×7.5 mm i.d., connected in series. A TSK SWP column (75 mm×7.5 mm i.d.) was used as a guard column. Mobilephase was 0.2M sodium acetate. Flowrate was 0.5 ml/min. Peaks were detected by refractive index measurements using heparin oligosaccharides of known sizes as reference.

A copper chelate affinity chromatography column was prepared as follows: Chelex 100 (Bio-Rad, 50 ml, 100–200 mesh) containing sodium ions was washed with water and packed in a column (2.6×30 cm). The Chelex gel was saturated with copper ions by pumping a solution of cupric ($Cu^{2+}$) chloride (0.5M; 500 ml) through the column at 3.8 cm/h. Excess cupric chloride was washed away with distilled water. The column was then equilibrated with sodium chloride (0.5M), containing sodium phosphate (0.02M). After the copper Chelex column, a column containing Chelex with sodium ions was placed. To this two column system, heparin fragment HF-4, obtained as described above (500 mg), dissolved in sodium chloride, sodium phosphate (0.5M, 0.02M) was applied. Heparin fragment which was only very little, or not at all retained on the copper chelex column was eluted with sodium chloride, sodium phosphate (0.5M, 0.02M). Elution was continued until no more fragment could be detected by UV at 214 nm. This fraction of heparin fragment HF-4 was called heparin fragment HF-5. After desalting on Sephadex G-15 and freeze-drying, the yield was 395 mg. The main peaks of this fraction on HPLC were tetradeca to hexadecasaccharides. Another fraction of heparin fragment which was retained by (bound to) the copper Chelex column was eluted by ammonium chloride (2M) containing sodium chloride (0.5M). After chromatography on Sephadex G-15, a yield of 0.7 mg was obtained. This fraction of heparin fragment was called heparin fragment HF-6. According to HPLC it consisted mainly of octa- to hexadecasaccharides.

EXAMPLE 4

Copper binding heparin fraction from standard sodium heparin

A copper Chelex column (5×25 cm) containing about 500 ml of copper ion containing gel was prepared according to Example 3. After that column, a sodium Chelex column (1.6×10 cm) was placed. To this two column system, a standard sodium heparin USP (20 g, anti-Xa 138 U/mg, H-1) dissolved in sodium chloride (0.5M) was added. Heparin that was only little, or not at all retained by the copper ions on the gel, was eluted with sodium chloride (0.5M, 1.8 l). When a stable baseline was obtained (UV-detection at 214 nm), elution was continued using aqueous ammonia (2M) containing sodium chloride (0.5M).

A portion of the heparin fraction that was not at all, or very little retained was treated with Chelex containing sodium ions and then freeze-dried (heparin fraction H-2). The retained heparin fraction was evaporated, desalted on Sephadex G-15, freeze-dried and treated with Chelex containing sodium ions and then desalted on Sephadex G-15 using distilled water. After freeze-drying, a heparin fraction (heparin fraction H-3) was obtained that had been retained on the copper Chelex column (88 mg). Anti-Xa activity was 119 U/mg. By elemental analysis N was 2.1%, S was 10.7%, Na was 10.3%, and Cu 220 ppm. The only amino sugar in this fraction according to amino acid analysis was glucosamine. Uronic acids were 28±3% w/w as determined by the carbazol sulfuric acid method according to Bitter and Muir, Anal. Biochem. 4, (1962) 330. The uronic acid content of the standard sodium heparin used as starting material was 30±3% w/w.

EXAMPLE 5

Preparation of a copper-binding tetrasaccharide fraction from heparin fragment obtained by partial depolymerization of sodium heparin by nitrous acid Depolymerized heparin from Example 3 was precipitated by adding 8 volumes of thanol. 5 g of the product thus obtained was dissolved in water, 12 ml, and subjected to gel permeation chromatography on a Biogel P-6 gel, 180×5 cm, with 0.25M sodium chloride as an eluent at 3.7 cm/h. Chromatography was monitored by a refractive index detector and fractions were pooled to obtain size homogenous oligosaccharides. The respective fractions were concentrated. The smaller size fractions were desalted by chromatography on a Sephadex G-10 column (85×5 cm) with water at 3.6 cm/h as an eluent. Detection of carbohydrate containing material was performed by a refactive index detector. Larger sized oligosaccharides ($\geq 10$ monosaccharide units) were desalted by ultrafiltration in a Amicon 8400 cell with a YCO5 filter. The yields were as follows:

| | |
|---|---|
| Tetrasaccharides | 0.51 g |
| Hexasaccharides | 0.71 g |
| Octasaccharides | 0.35 g |
| Decasaccharides | 0.51 g |
| Dodecasaccharides | 0.17 g |
| Tetradecasaccharides | 0.31 g |
| Hexadecasaccharides | 0.15 g |
| Octadecasaccharides | 0.14 g |
| Eicosasaccharides and larger saccharides | 0.43 g |

The tetrasaccharide fraction (6.0 g) (TS-4) was dissolved in water (10 ml) and applied to a Chelex 100 column (25×1.6 cm), copper form. Water at 1.2 cm/h was used as an eluent to obtain a fraction with low affinity for copper. Detection was performed with a ultraviolet UV 214 detector. When the first fraction was eluted, the eluent was changed to ammonia (1,000 ml, 2M) and a second fraction was collected. The respective fractions were concentrated and then treated with Chelex 100, sodium form. Finally the fractions were chromatographied on Sephadex G-10 with water at 3.6 cm/h as an eluent to give the nonbinding fraction (5.8 g) (TS-5) and binding fraction (84 mg).

The binding fraction was dissolved in 0.25M sodium chloride and applied to gel permeation chromatography on a Biogel P-6 gel, 180×5 cm column and eluted with 0.25M sodium chloride as above. The tetrasaccharide fraction was collected and desalted on Sephadex G-10 with water as an eluent to give, after freeze-drying, 70 mg product with a copper content of 3,900 ppm (TS-6). The binding fraction (18 mg) was dissolved in water (5 ml) and sodium chloride (20 mg) and Chelex 100 was added. The mixture was left for two hours and then filtered. After concentration the remainder was desalted on a G-10 column as above. The tetrasaccharide was collected and freeze-dried to give 9.5 mg product with a copper content of 2,900 ppm (TS-7). The tetrasaccharidic nature of TS-7 was confirmed by HPLC gel permeation chromatography according to example 3.

EXAMPLE 6

A hexasaccharide fraction (HS-4) prepared according to example 5 (1.15 g) was dissolved in 0.5M sodium chloride and applied to a two column system consisting of a copper Chelex column followed by a sodium Chelex column. The columns were eluted by a stepwise increasing concentration of ammonium chloride. Each fraction was desalted by repeated chromatography on Sephadex G-15 then treated with a large excess sodium chloride and desalted again yielding the following fractions. Fractions HS-5 and HS-9 were further purified by treatment with sodium Chelex.

| Fraction no | Eluent | Volume (ml) | Yield (mg) | Cu-content (ppm) |
|---|---|---|---|---|
| HS-5 | 0.5 M NaCl | 270 | 897 | 18 |
| HS-6 | 0.5 M NaCl 0.7 M NH₄Cl | 500 | 75 | 550 |
| HS-7 | 0.5 M NaCl 1.4 M NH₄Cl | 340 | 10 | 120 |
| HS-8 | 0.5 M NaCl 2.0 M NH₄Cl | 780 | 32 | 640 |
| HS-9 | 0.5 M NaCl 3.0 M NH₄Cl | 700 | 4 | 425 |

Fractions HS-9 was confirmed by HPLC gel-permeation chromatography to be a hexasaccharide. A1H-NMR spectrum is shown in FIG. 1.

EXAMPLE 7

Chelating Sepharose 6B (Pharmacia; 110 ml) was placed in a beaker. Cupric ($Cu^{2+}$) sulfate (0.5M, IL) was added and the gel was left over night. The copper-ion containing gel was filtered on a sintered glassfunnel and thoroughly washed with water (10 l). It was than added to a sodium chloride solution (1M, 300 mL) containing sodium phosphate (0.1M; pH 7.5), (buffer A). The gel was deaerated and transferred to a chromatography column (40×2.6 cm) and washed with buffer A (100 mL). A decasaccharide (DS-1) obtained according to example 5 (5 g) was dissolved in buffer A (15 mL) and placed on the top of the copperion containing column. Elution was performed with buffer A at 6.8 cm/h. The eluate was monitored with a fixed wavelength UV detector (UV-214, Pharmacia), and fractions were collected (20 min/tube). After 30 min a non-binding material emerged. Fractions containing the non-binding material was pooled and concentrated, desalted and freeze-dried to give decasaccharide DS-2. The copper column was then washed with sodium chloride (3M) containing sodium phosphate (0.1M, pH 7.5) buffer B at 6.8 cm/h for 7 h. No peaks appeared in the chromatogram during this period. The eluent was then changed to ammonium chloride (2M) and chromatography was continued until a peak emerged. Fractions corresponding to this peak were collected and pooled, concentrated and desalted in an Amicon 8000 ultrafilter cell using a YCO 5 membrane. The retentate was washed with sodium chloride (1M, 2×300 mL) and then with water until free from chloride ions. The retentate was freeze-dried to give a binding fraction (DS-3), 14 mg, Cu content 640 ppm. No further peaks appeared on continued chromatography with 2M ammonium chloride over night.

BIOLOGICAL TESTS

The angiogenic response of the chorioallantoic membrane (CAM) to heparin, heparan sulfate or products containing heparin and/or heparan sulfate constituents were investigated on fertilized eggs. Non-incubated (0-day) fertilized eggs obtained from Linköpings Kontrollhönseri, Linköping, Sweden were stored in a low temperature incubator 13°–17° C. until ready for incuation at 37° C. in an Egg Incubator (Andersson & Bonde TYP 40). Incubated eggs (37° C.) are cracked on the 3rd day of incubation (3-day) and the entire content is poured into a Petri dish. Only eggs with unbroken yolk were used for further incubation in a $CO_2$ tissue culture incubator with 3% $CO_2$ at 37° C. with elevate relative humidity. After 3 days incubation (6-day) in $CO_2$ atmosphere the eggs are implanted with a methyl cellulose dish prepared as described below. Methyl cellulose is added to triple distilled water at a concentration of 0.5%, then auto-claved 30 minutes at 138 kPa and 120° C. for sterility. This mixture will contain a ball of gelled methyl cellulose. Subsequent slow agitation for 2–3 days at 5° C. insures complete dissolving of solution. The solution is then kept in a refrigerator until ready for use. The test material is suspended in the methyl cellulose solution at room temperature to a final concentration of 5 to 50 $\mu g/10$ $\mu l$. Aliquots of 10 $\mu l$ methylcellulose containing the test sample, are deposited onto the end of a teflon rod (3 mm diam.). When the methyl cellulose test material disc is dry (30–40 min) it is lifted off the teflon with 2 fine forceps and placed on the peripheral part of a 6-day CAM in order to avoid non-growing vessels. On day 8 the growing vessels under and around the transparent disc are examined under a dissecting microscope (×26 to ×40 magnification). The inhibition of vessel growth is scored either as no inhibition of vessel growth or as inhibiting vessel growth. Each compound is tested at a minimum of 15 eggs and the scoring is performed by two technicians who are uninformed concerning the nature and concentration of the test substance.

The results are expressed as per cent eggs showing inhibition.

EXAMPLE 9

Copper content of fractions of heparin fragments of the invention (Table 2)

Heparin fragments HF-1, HF-2 and HF-3 were analyzed for copper by atomic absorption spectroscopy. They were found to contain 9 ppm, 5 ppm and 255 ppm, respectively. Further treatment of a solution of heparin fragment HF-3 in distilled water with Chelex 100 containing sodium ions did not give any decrease in the copper content. In order to reduce the copper content below 10 ppm, the following steps were employed. For all the steps carried out, a Diaflo membrane 5YCO5 in an Amicon 8050 ultrafilter cell was used.

Heparin fragment (HF-3) was dissolved in sodium chloride (2M, 50 ml) and washed by additional sodium chloride (2M; 250 ml) and then by distilled water (200 ml) and then freeze-dried. This freeze-dried fragment was then dissolved in ethylendiaminetetraacetic acid (EDTA; 0.1M; pH 7.0; 50 ml) and washed with an additional 250 ml of the same solution. It was then successively washed with sodium chloride (1M, 250 ml) and distilled water (250 ml) and then freeze-dried. This freeze-dried fragment was once more treated in the same way using twice the washing volumes and then freeze-dried. The heparin fragment called HF-3A, now had a copper content of 5 ppm. All the freeze-dried intermediates above were analyzed for copper but only after all steps the copper content was below 10 ppm.

For addition of copper ions to heparin fragment HF-3A a stock solution of cupric($Cu^{2+}$)chloride was prepared as follows: Cupric($Cu^{2+}$)chloride×$2H_2O$ (27.1 mg) was weighed into a graduate flask and triple distilled water was added to the mark, 10 ml. From this solution 1 ml was drawn into a second graduate flask and triple distilled water was added to the mark, 1,000 ml. This solution contained 1.01 $\mu g$ Cu/ml $H_2O$. 5.2 mg of heparin fragment containing 5 ppm of copper (HF-3A) was dissolved in triple distilled water (2.0 ml). 0.51 ml of the stock solution was added and the mixture was left at room temperature for 4 hours and then freeze-dried to give heparin fragment HF-3B. The copper content by atomic absorption analysis was 100 ppm.

Heparin fragment HF-3A (5.9 mg) was dissolved in triple distilled water (2.0 ml) and 3.80 ml of the stock solution was added and the mixture was left at room temperature for 4 hours and then freeze-dried to give heparin fragment HF-3C, the copper content by atomic absorption analysis was 645 ppm.

Heparin fragment HF-3A (4.6 mg) was dissolved in 2.0 ml of triple distilled water and 6.90 ml of the stock solution was added and the mixture was left for 4 hours at room temperature and then freeze-dried to give heparin fragment HF-3D. The copper content by atomic absorption was 1,500 ppm.

HF-3C (3.6 mg) and HF-3D (4.1 mg) was dissolved in water (10 ml). The solution was then freeze-dried to give heparin fragment HF-3E (7.6 mg) containing 1100 ppm Cu as determined by atomic absorption.

For addition of copper ions to heparin fragment HF-2, 20.0 mg of HF-2 was dissolved in 2.0 ml triple distilled water and 3.17 ml of the stock solution was added and the mixture was left at room temperature for 4 hours and then freeze-dried to give heparin fragment HF-2A. The copper content by atomic absorption spectroscopy was 160 ppm.

The fractions of heparin were treated in the same way as the fractions of the heparin fragments in order to give the heparin fractions H-3A, H-3B, H-3C and H-2A.

It is seen in Table 2 that the anti-angiogenic effect is almost totally lost when the copper content is reduced. For example, the percent inhibition is 8 for fragment HF-3A compared with 57 for fragment HF-3. Addition of copper ions restored the activity, as is seen e.g. in fragments HF-3B, HF-3D, and HF-3E exhibiting 37, 70, and 53% inhibition, respectively. A similar effect as for heparin fragments is seen also for Heparin, compare H-3A and H-3B with H-3 in Table 2.

We claim:

1. A novel complex of
   (a) a metal ion selected from copper, calcium, manganese, iron, and zinc ions, and
   (b) a fraction of heparin, heparan sulfate, low molecular weight heparin, low molecular weight heparan sulfate, heparin fragments, heparan sulfate fragments, and oligosaccharides derived from heparin or from heparan sulfate, or a salt of such fractions, which fractions bind to the said metal ion,
   said complex containing from 5 to 1,000 nmole metal per μmole of component (b).

2. A complex according to claim 1 wherein component (a) is copper ions.

3. A complex according to claim 2 wherein the amount of copper is from 10 to 1,000 nmole per μmole of component (b).

4. A complex according to claim 2 wherein component (b) is heparin or a low molecular weight heparin or a heparin fragment or an oligosaccharide derived from heparin.

5. A complex according to claim 4 wherein the said oligosaccharide is a tetrasaccharide, a hexasaccharide, an octasaccharide, a decasaccharide, a dodecasaccharide, a tetradecasaccharide, or a hexadecasaccharide.

6. A complex according to claim 2 wherein component (b) is heparan sulfate or a low molecular weight heparan sulfate or a heparan sulfate fragment or an oligosaccharide derived from heparan sulfate.

7. A complex according to claim 6 wherein the said oligosaccharide is a tetrasaccharide, a hexasaccharide, an octasaccharide, a decasaccharide, a dodecasaccharide, a tetradecasaccharide, or a hexadecasaccharide.

8. A complex according to claim 1 wherein the component (b) of claim 1 is in the form of a salt.

9. A complex according to claim 8 wherein the salt is a sodium or a calcium salt.

10. A complex according to claim 9 wherein the salt is a sodium salt.

11. A process for the preparation of a complex according to claim 1 consisting of adding heparin, heparan sulfate, low molecular weight heparin, low molecular weight heparan sulfate, a heparin fragment, a heparan sulfate fragment, an oligosaccharide derived from heparin or heparan sulfate to a solid matrix containing a metal ion selected from copper, calcium, manganese, iron and zinc ions, separating the fraction of added material that does not bind to the ions on the matrix and isolating the fraction bound to the metal ions on the matrix.

12. A process according to claim 11 wherein the metal ion component (a) is copper ions and wherein the isolation of the complex is carried out by using an ion exchange matrix containing iminodiacetic acid groups.

13. A pharmaceutical composition comprising as active ingredient a complex according to claim 1.

14. A method for reducing angiogenesis in an animal or human host in need of such treatment, comprising administration of a therapeutically effective amount of a complex according to claim 1 in conjunction with an angiostatic component, especially a so-called angiostatic steroid component.

15. The process of claim 11 wherein the separation comprises desorption from the metal-ion containing solid matrix by a member selected from the group consisting of pH gradient, competitive ligand and chelating agent.

16. The process of claim 15 wherein said metal ion component is copper.

17. A fraction of heparin, heparan sulfate, low molecular weight heparin, low molecular weight heparan sulfate, heparin fragments, heparan sulfate fragments, or of an oligosaccharide derived from heparin of from heparan sulfate, or a salt of such fractions, having the capacity to bind per μmole, from 5 to 1,000 nmole of metal ions selected from copper, calcium, manganese, iron, and zinc ions.

* * * * *